(12) United States Patent
Chikkali et al.

(10) Patent No.: US 10,266,621 B2
(45) Date of Patent: Apr. 23, 2019

(54) METAL-PHOSPHINESULFONATE ACETONITRILE COMPLEX FOR INSERTION COPOLYMERIZATION OF FUNCTIONAL OLEFINS

(71) Applicant: Council of Scientific and Industrial Research, New Delhi (IN)

(72) Inventors: Samir Hujur Chikkali, Pune (IN); Shahaji Rajaram Gaikwad, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/510,608

(22) PCT Filed: Sep. 10, 2015

(86) PCT No.: PCT/IN2015/050107
§ 371 (c)(1),
(2) Date: Mar. 10, 2017

(87) PCT Pub. No.: WO2016/038631
PCT Pub. Date: Mar. 17, 2016

(65) Prior Publication Data
US 2017/0362352 A1     Dec. 21, 2017

(30) Foreign Application Priority Data

Sep. 10, 2014   (IN) .......................... 2587/DEL/2014

(51) Int. Cl.
*C08F 10/02*     (2006.01)
*C07F 9/50*      (2006.01)
*C07F 15/00*     (2006.01)

(52) U.S. Cl.
CPC ............ *C08F 10/02* (2013.01); *C07F 9/5022* (2013.01); *C07F 15/006* (2013.01)

(58) Field of Classification Search
None
See application file for complete search history.

(56) References Cited

FOREIGN PATENT DOCUMENTS

WO    WO-200006615      2/2000
WO    WO-2016/038631    3/2016

OTHER PUBLICATIONS

Drent, Eite, et al., "Palladium catalysed copolymerisation of ethene with alkylacrylates: polar comonomer built into the linear polymer chain", Chem. Commun., 744-745, (2002), 744-745.

(Continued)

*Primary Examiner* — Clinton A Brooks
(74) *Attorney, Agent, or Firm* — Schwegman Lundberg & Woessner, P.A.

(57) ABSTRACT

The present invention discloses nitrile ligated transition metal-phosphinobenzene-sulfonate complex of formula (I) as catalyst for insertion-copolymerization of mono and bis functionalized vinyl monomers with ethylene or other olefins. In particular, the present invention discloses nitrile ligated metal-phosphinobenzene-sulfonate complex of formula (I) as catalyst for insertion-copolymerization of mono and bis functionalized vinyl monomers with ethylene and or other olefins and to the process for preparation thereof. The invention further discloses a process for the insertion-(co)polymerization of mono and bis functionalized vinyl monomers with olefins catalyzed by the catalyst of formula (I).

(Continued)

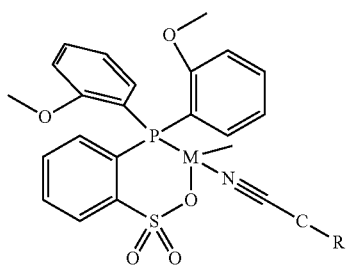

Formula I

9 Claims, 9 Drawing Sheets

(56) References Cited

OTHER PUBLICATIONS

Friedberger, Tobias, et al., "Mechanistic Insights into Polar Monomer Insertion Polymerization from Acrylamides", *J. Am. Chem. Soc.*, 134(2), (2012), 1010-1018.

Gaikwad, Shahaji R., et al., "Insertion Copolymerization of Difunctional Polar Vinyl Monomers with Ethylene", *ACS Macro Lett.*, 4(9), (2015), 933-837.

Guironnet, Damien, et al., "Insertion Polymerization of Acrylate", *J. Am. Chem. Soc.*, 131(2), (2008), 422-423.

Ittel, Steven D., et al., "Late-Metal Catalysts for Ethylene Homo- and Copolymerization", *Chem. Rev.*, 100(4), (2000), 1169-1204.

Kochi, Takuya, et al., "Olefin Polymerization with Methylpalladium Complexes Bearing Phosphine-Sulfonate Bidentate Ligands", *Polymer Preprints*, 47(2), (2006), 582-583.

Kochi, Takuya, et al., "Synthesis of anionic methylpalladium complexes with phosphine-sulfonate ligands and their activities for olefin polymerization", *Dalton Trans.*, (2006), 25-27.

Rünzi, Thomas, et al., "Reactivity of Methacrylates in Insertion Polymerization", *J. Am. Chem. Soc*, 132(46), (2010), 16623-16630.

"International Application No. PCT/IN2015/050107, International Preliminary Report on Patentability dated Nov. 10, 2016", (Nov. 10, 2016), 17 pgs.

"International Application No. PCT/IN2015/050107, International Search Report and Written Opinion dated Jan. 13, 2016", (Jan. 13, 2016), 9 pgs.

Anselment, Timo Martin Jürgen, "Development of Novel Phosphine Sulphonate-Based Palladium Catalysts for Ethene Homo- and Co-Polymerisation Reactions with Polar-Functionalised Olefins", Thesis Paper, Technische Universität München, (Jun. 17, 2011), 197 pgs.

SCHEME 1

METAL-PHOSPHINESULFONATE ACETONITRILE COMPLEX FOR INSERTION COPOLYMERIZATION OF FUNCTIONAL OLEFINS

PRIORITY CLAIM TO RELATED APPLICATIONS

This application is a U.S. national stage application filed under 35 U.S.C. § 371 from International Application Serial No. PCT/IN2015/050107, which was filed 10 Sep. 2015, and published as WO2016/038631 on 17 Mar. 2016, and which claims priority to India Application No. 2587/DEL/2014, filed 10 Sep. 2014, which applications and publication are incorporated by reference as if reproduced herein and made a part hereof in their entirety, and the benefit of priority of each of which is claimed herein.

TECHNICAL FIELD OF THE INVENTION

The present invention relates to nitrile ligated transition metal-phosphinobenzene-sulfonate complex of formula (I) as catalyst for insertion-copolymerization of mono and bis functionalized vinyl monomers with ethylene or other olefins and process for the preparation thereof. The invention further relates to a process for the insertion-(co)polymerization of mono and bis functionalized vinyl monomers with olefins catalyzed by the complex of formula (I).

BACKGROUND OF THE INVENTION

Polymers form a major part of chemicals produced and used every day. Owing to their importance, polymerization techniques have developed rapidly over the years. A tremendous progress has been made and today the world produces roughly 145 million tons of polyolefins annually. Polyethylene (PE) occupies the top position (in terms of production) among the polyolefins and various grades of PE are commercially produced for numerous applications.

Further, the introduction of Ziegler Natta catalyst was a breakthrough for production of large variety of polymeric material such as high density polyethylene (HDPE) and isotactic polypropylene on commercial scale. The oxophilicity of early transition metal based Ziegler-Natta type catalysts and coordination of the functional group on the polar vinyl monomer to the metal (occupying the vacant site) generally lead to catalyst poisoning and the problem was addressed by post-functionalization of PE, Acyclic diene metathesis (ADMET) polymerization of functionalized diener or organometallic mediated radical polymerization of polar vinyl monomers with ethylene. These methods suffer from typical issues associated with free radical polymerization, poor control over branching, molecular weight, molecular weight distribution etc.

Polyethylene (PE) is inherently a long-chain of hydrophobic methylene repeat units without any functional groups on the backbone. This partly limits the potential application of PE in adhesives, binders, paints, printing ink, dyeing etc. Incorporation of even small amount of functional groups in PE can significantly enhance these material properties and can further broaden the PE application.

Incorporation of small amount of functional groups is now realized by 'co-ordination-insertion polymerization'. The mechanism includes the migratory insertion of a coordinated olefin into a metal alkyl bond via a four membered transition state.

A very promising approach in the use of effective late transition metal catalysts for olefin polymerization especially acrylate units was reported by Brookhart et.al (Chem. Rev. 2000, 100, 1169) using Pd or Ni complexes with bulky α-diimine ligands. Although the initial results were encouraging, problems like high degree of branching, low monomer incorporations and catalyst degradation at higher temperature, limited the use of these catalysts.

Due to the relatively low Lewis acidity of late transition metal olefin polymerization catalysts, neutral complexes, mostly based on Pd(II), are usually regarded as the most promising perspectives in homo- or co-polymerization reactions of functionalized olefins.

The innovative ligand design has helped overcome some of these shortcomings. The ligand system comprising of phosphine-sulfonate system (Drent and co-workers in Chem. Commun. 2002, 744;) displayed broad functional group tolerance and various polar vinyl monomers such as acrylate, acrylonitrile, vinyl acetate, vinyl ethers, acrylic acid and vinyl chloride that could be incorporated.

An article titled "Synthesis of anionic methylpalladium complexes with phosphine-sulfonate ligands and their activities for olefin polymerization" by Kenji Yoshimura et. al published in Dalton Transactions, 2006, 25-27 reports copolymerization of ethylene and methyl acrylate with the anionic methylpalladium complexes and the effects of additives on the catalytic activity and further concludes that further examination of additives, ligands, bases used to prepare the catalysts and reaction conditions are required to provide an improved catalyst system for production of the unique highly linear copolymer of ethylene and methyl acrylate.

Another article titled "Olefin polymerization with methylpalladium complexes bearing phosphine-sulfonate bidentate ligands" by Takuya Kochi, et al. (Polymer Preprints 2006, 47(2), 582) reports copolymerization of Ethylene with Methyl Acrylate using methylpalladium complexes bearing phosphine-sulfonate bidentate ligands to produce linear copolymers similar to those obtained with Pugh's catalyst system.

The excellent performance of phosphinesulfonate system further raised the scientific aspirations and subsequent investigations were focused on structural fine-tuning. Recently the dependence of the polymerization activity on basicity of the employed ligand is reported by Mecking et al. (in J. Am. Chem. Society 2009, 131, 422) with introduction of dimethylsulfoxide (DMSO) into a phosphine sulfonate catalyst. However, when this catalyst is applied for polymerization of ethylene in the presence of methyl methacrylate, at variable concentrations, yielded ethylene homopolymer exclusively. (JACS 132, 2010, 46, pp, 16623-16630). Further, higher monomer concentrations are required during polymerization to give poly(ethyleneco-MA) with over 50 mol % MA content using these complexes as catalyst. Therefore, it appears that there is a limitation for the applicability of this catalyst for ethylene copolymerization reactions.

Similarly, the polymerization activities are reported in the art with the use of bases such as pyridine, lutidine into a phosphine sulfonate catalyst.

Thesis titled 'Development of Novel Phosphine Sulfonate-Based Palladium Catalysts for Ethene Homo- and Co-Polymerisation Reactions with Polar-Functionalised Olefins' by Timo Martin (2011) discloses the use of Non-Symmetrically Sulfonated Phosphine Ligands in ethene homo and co-polymerization reaction with polar functionalised olefins such as acrylonitrile's, allyl nitriles, acrylates etc. The thesis further discusses the effect of structural modification of sulfonated phosphine ligand such as introduction of a para-methyl group (respective to the sulfonate) or alteration of the aryl substituents at phosphorus, for example by exchange of the functionalities in ortho-position by the introduction of ortho-Me or ortho-Et groups instead of ortho-OMe groups, addition of coordinating solvents such as pyridine, DMSO acting as Lewis bases on the activity of the catalyst and on the insertion-copolymerization process to obtain high molecular weight polymers and copolymers.

A PCT publication bearing no.WO/2000/06615 relates to a process for the polymerization of ethene and optionally one or more other olefin monomers by contacting the monomers under polymerization conditions with a catalyst system obtainable by combining: (a) a palladium, nickel or platinum ion, (b) an anion derived from an acid having a pKa of less than 3, and containing an atom of Group V A of the Periodic Table of Elements, wherein the Group VA atom is substituted with at least one aryl group, said aryl groups being substituted with a polar group on the ortho position.

Insertion copolymerization of various mono-functionalized polar vinyl monomers and mono-functionalized allylic monomers are accomplished in the art, however, insertion copolymerization of industrially relevant bis-functionalized vinyl monomers yet remains to be explored.

There are two fundamental challenges in the insertion copolymerization of such bis-functionalized vinyl monomers; a) the C-C double bond is extremely electron poor (due to the two electron withdrawing groups) and the olefin is sterically even more demanding than the mono-functionalized vinyl monomers.

To overcome the above challenges, the present inventors felt it would be prudent to introduce a weak coordinating group at the fourth coordination site in the catalyst system. This is achieved by providing acetonitrile in the catalyst system which not only acts as a catalyst but also enables the incorporation of two functional groups such as a cyano group (—CN) and ester group (—COOMe) in to the ethylene monomer during co-polymerization, which has not been demonstrated in the art hitherto.

Therefore, there remains a need in the art to provide a catalyst that works effectively for insertion copolymerization of olefin with mono or bis-functionalized polar vinyl monomers to give comfortable and consistent yields of copolymers.

OBJECTS OF THE INVENTION

Main object of the present invention is to provide a nitrile ligated Metal-phosphinobenzene-sulfonate complex of formula (I) as catalyst for insertion-copolymerization of mono functionalized and bis-functionalized polar vinyl monomers with ethylene.

Yet another object of the present invention is to provide a simple and cost effective process for preparation of nitrile ligated Metal-phosphinobenzene-sulfonate complex of formula (I).

Yet another object of the present invention is to provide nitrile ligated Pd-phosphinobenzene-sulfonate complex of formula (3) and a process for the preparation thereof.

Yet another object of the present invention is to provide an effective insertion-copolymerization to obtain a copolymer of poly (ethylene-mono functionalized and bis-functionalized polar vinyl monomers) using Metal-phosphinobenzene-sulfonate complex of formula (I).

SUMMARY OF THE INVENTION

Accordingly, present invention relates to a complex of formula (I)

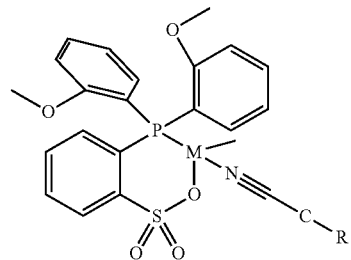

Formula I wherein metal 'M' is selected from the group consisting of Pd, Pt, Ni, Ru; preferably Pd; and R is selected from the group consisting of (un)substituted or substituted alkyl in the range of (C1 to C5) or aryl.

In an embodiment of the present invention, representative complex comprising:

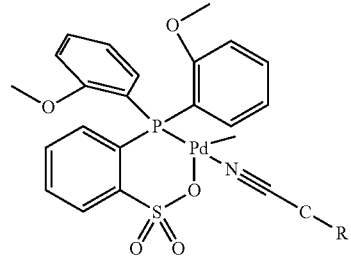

Formula 3

In another embodiment of the present invention, said complex is crystallized in orthorhombic space group with cell parameters a=16.3061(7)Å b=16.4145(7)Å c=19.0195(8)Å.

In another embodiment, present invention provides a one-step process for preparation of complex of formula (I) comprising:

a) mixing sodium-salt of phosphinesulfonate ligand (1) and reagent at room temperature in the range of 25-40° C. followed by adding acetonitrile at same temperature to obtain the nitrile ligated Pd-phosphinobenzene-sulfonate complex of formula (I).

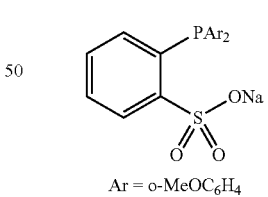

Ar = o-MeOC₆H₄

Yet another embodiment of the present invention, reagent used is selected from the group consisting of cyclooctadienyl-palladium-methylchloride, Tetrametylethylenediamine-Nickel-dimethyl,Tetrametylethylenediamine-Nickel-dichloride, Tetrametylethylenediamine-palladium-methylchloride, Tetrametylethylenediamine-Platinium-dimethyl,Tetrametylethylenediamine-Platinium-dichloride or cyclooctadienyl-ruthenium-dichloride.

In another embodiment, present invention provides a one-step process for preparation of complex of formula (I) optionally comprising:

i. adding AgBF4 to [({(P^O)Pd(Me)Cl}μ-Na)2](2) followed by adding acetonitrile and in dichloromethane and stirring the mixture at room temperature in the range of 25-40° C. to obtain the nitrile ligated Pd-phosphinobenzene-sulfonate complex of formula (I).

In yet another embodiment of the present invention, said complex is useful as a catalyst in insertion copolymerization of mono functionalized and bis functionalized polar vinyl monomers with olefin for preparation of copolymer of formula II;

(A-B)n,                                           Formula II wherein
n=10-10000;
A is an olefin selected from ethene, propene, butene, styrene and the like; preferably ethylene;
B is selected from mono functionalized and bis functionalized polar vinyl monomers are selected from acrylates, acrylic acid, acrylonitrile, ethyl-2-cyanoacrylate, methyl-2-cyanoacrylate, trifluoromethyl acrylic acid, allyl acetate, allyl alcohol, allyl amine and the like;
and the said process comprising the step of:
i. reacting an olefin with mono functionalized and/or bis functionalized polar vinyl monomers in presence of complex of formula (I) in solvent at a temperature in the range of 45-110° C. and at pressure in the range of 1-20 bars to obtain copolymer of formula II.

In yet another embodiment of the present invention, solvent used is selected from the group consisting of toluene, xylene, cyclohexane, hexane and the like.

In yet another embodiment of the present invention, the concentration of the vinyl monomer is in the range of 0.001 to 10.0 mol/lit.

In yet another embodiment of the present invention, the copolymers of formula II are selected from:
a) poly(ethylene-ethyl-2-cynoacrylate)
b) poly(ethylene-acrylonitrile)
c) poly(ethylene-methyl acrylate)
d) poly(ethylene-trifluoromethyl acrylate).
e) poly(ethylene-trifluoromethyl acrylic acid).

DETAILED DESCRIPTION OF THE INVENTION

Figure 1:
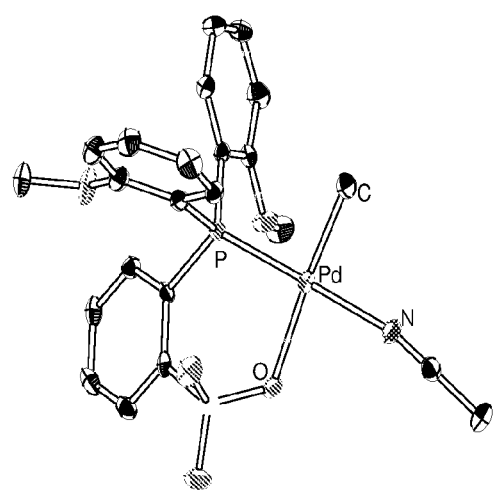
FIG. 1 depicts Molecular structure of complex 3; solvent molecules and H-atoms are omitted for clarity; thermal ellipsoids are drawn at 50% probability level.

Present invention provides a catalyst system by fine tuning the structure of phosphinesulfonate system due to which optimization of the functional group incorporation as well as the enhancement of the catalyst activity in the polymerization reactions of olefin with both mono functionalized and bis-functionalized polar vinyl monomers can be achieved.

One of the prerequisite of chain growth polymerization is π-coordination of a monomer and easy removal of the labile group at equilibrium. To achieve these objectives, the present inventors have fine-tuned the structure of metal-phosphinobenzene-sulfonate by providing a weak coordinating group at the fourth coordination site of the complex that can mimic the donor atom of the polar vinyl monomer in insertion-copolymerization process.

Introducing weak coordinating group 'acetonitrile' at the fourth coordination site in the neutral phosphine-sulfonato catalyst system of the present invention not only catalyzes the insertion copolymerization of ethylene with 1,1-di-substituted di-functional olefin but also provides a novel class of functional polyolefins with two functional moieties (cyano-acrylate or Fluoro-acrylic acid) incorporated at a time.

Further, polymer of cyano-acrylate which is known as super glue is commercially used in applications such as binders, adhesives etc. But the current method to polymerize this monomer uses radical reactions, which are uncontrolled and lead to undefined polymers. Moreover, the monomer itself is costly compared to ethylene.

The present method enables insertion copolymerization of industrially relevant bis-substituted polar vinyl monomer such as cyano-acrylate (super glue) into linear ethylene chain using the novel catalyst system, wherein, said catalyst system tolerates di-functional vinyl monomers and provides direct access to di-functional polyolefins and produce functional copolymers with reasonable molecular weights.

Present invention provides a nitrile ligated transition metal-phosphinobenzene-sulfonate complex of formula (I) as catalyst useful for insertion-copolymerization of mono functionalized and bis functionalized polar vinyl monomers with ethylene comprising:

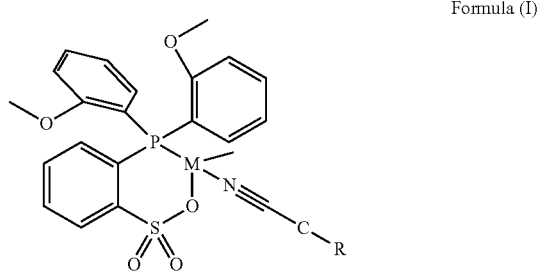

Formula (I)

wherein M is selected from the group consisting of Pd, Pt, Ni or Ru; preferably Pd; and
R is selected from the group consisting of (un)substituted or substituted alkyl (C1 to C5) or aryl.

The present invention discloses nitrile ligated Pd-phosphinobenzenesulfonate-acetonitrile complex (3) useful for insertion-copolymerization of mono functionalized and bis functionalized polar vinyl monomers with ethylene.

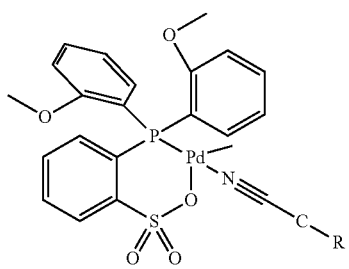

Formula 3

The present invention discloses the simple one step process for preparation of nitrile ligated Pd-phosphinobenzene-sulfonate complex of formula (II).

Accordingly, in the direct synthesis method, to the mixture of sodium-salt of phosphine sulfonate ligand (1) and cyclooctadienyl-palladium-methyl chloride, acetonitrile was added and the mixture was stirred at room temperature (25 to 40° C.) to obtain a clear solution. The clear solution was filtered and the filtrate passed through the celite bed, washed with acetonitrile, evaporated the volatiles of the filtrate under pressure to obtain a solid. The solid material was further washed with an organic solvent, dried under vacuum to obtain Pd-phosphinesulfonate-acetonitrile complex of formula (3).

Figure 8:
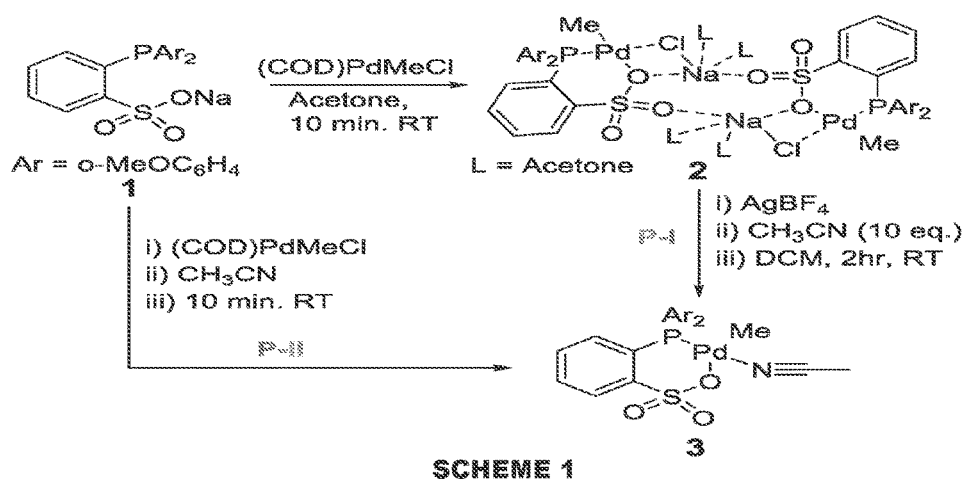
FIG. 8 represents the processes for the preparation of nitrile ligated Pd-phosphinobenzene-sulfonate complex of formula (I).

Alternately, the complex (3) was prepared from acetone-dimer (2) which is obtained from sodium-salt of ligand (1)(FIG. 8). To the acetone-dimer (2) was added $AgBE_4$ and a mixture of acetonitrile (10 equv) and DCM. The reaction mixture was stirred for about 2-4 hrs in dark at room temperature, filtered and washed to obtain the desired complex.

The processes for the preparation of nitrile ligated Pd-phosphinobenzene-sulfonate complex of formula (I) is depicted in FIG. 8.

Figure 7:
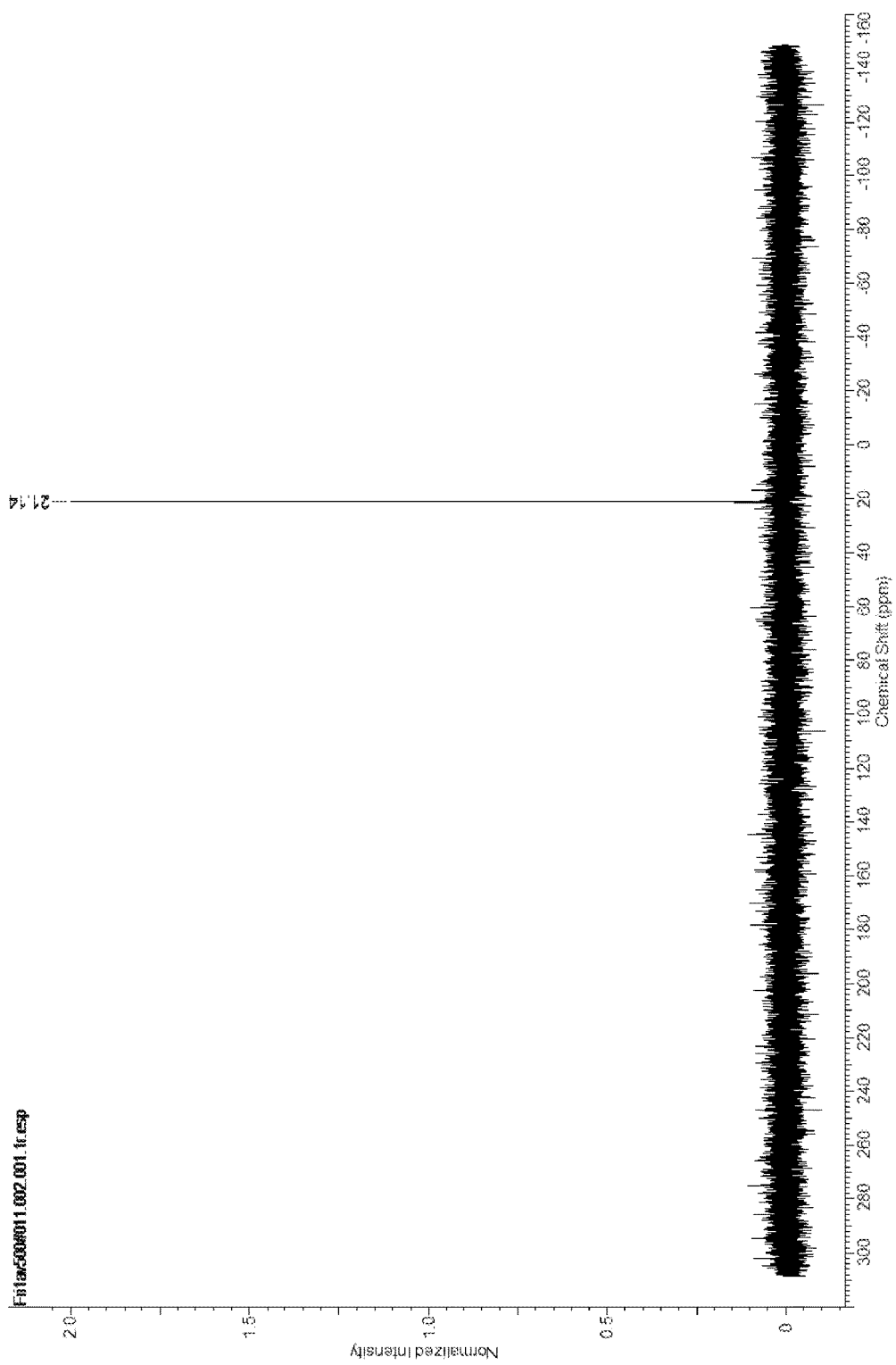
FIG. 7 depict $^{31}P$ NMR spectrum of complex 3 in $CDCl_3$ (500 MHz, 298K).

The existence of palladium complex (3) was ascertained from spectroscopic and analytical data. $^{31}P$ NMR of complex (3) displayed a characteristic resonance at 21.1 ppm (FIG. 7). In a typical proton NMR, the palladium bound methyl protons (Pd—$CH_3$) showed appearance at 0.18 ppm, whereas the corresponding methyl carbon (Pd—$CH_3$) appeared at −2.9 ppm in a $^{13}C$ NMR spectrum. The electrospray ionization mass spectrum (ESI-MS +ve mode) which pseudo-molecular ion peak at m/z=544.97 [M-ACN+Na]$^+$. A single crystal X-ray structure of complex (3) showed slightly distorted square planar geometry at palladium (FIG. 1) which is crystalized in orthorhombic Pbca space group. The phosphine and the methyl group were observed to be mutually cis to each other whereas, the acetonitrile is situated trans to the phosphine.

The comparative binding strength of the donor solvents were evaluated by adding one equivalent of DMSO into the complex 3 and the changes were tracked using proton and phosphorus NMR. Addition of 1 equivalent of DMSO lead to complete disappearance of a characteristic Pd-Me (in 3) resonance at 0.18 ppm, concomitantly a new signal at 0.39 ppm appeared in the $^1H$ NMR spectrum (in table 9 below). The new resonance (at 0.39) could be readily assigned to a previously reported DMSO coordinated Pd-Me complex [Guironnet, D.; Roesle, P.; Runzi, T.; Gottker-Schnetmann, I.; Mecking, S. J. Am. Chem. Soc. 2009, 131, 422].

The present invention discloses polymerization of ethylene using the catalyst of formula (I) wherein the ethylene pressure is in the range of 1-20 bar, the polymerization is carried in non-polar solvents selected from toluene, xylene, cyclohexane, hexane and the like.

The invention provides copolymerization of olefin and mono functionalized and bis functionalized polar vinyl monomers using the catalyst of formula (I). The olefin is selected from ethene, propene, butene, styrene and the like; preferably ethylene. The mono functionalized and bis functionalized polar vinyl monomers are selected from acrylates, acrylic acid, acrylonitrile, cyano-acrylate, trifluoromethyl acrylic acid, allylacetate, allylalcohol, allylamine and the like.

The solvent for copolymerization reaction is selected from non-polar solvents such as toluene, xylene, cyclohexane, hexane and the like. The temperature is in the range of 45-110° C.; the pressure is maintained at about 5 bar; the concentration of the vinyl monomer is in the range of 0.001 to 10.0 mol/lit The present invention discloses the co-polymer of formula II obtained by the process in accordance with the present invention, comprising:

(A-B)n            Formula (II)

wherein A is selected from the group consisting of ethene, propene, butene, styrene and the like; preferably ethylene;

B is selected from mono functionalized and bis functionalized polar vinyl monomers, wherein mono functionalized and bis functionalized polar vinyl monomers are selected from acrylates, acrylic acid, acrylonitrile, ethyl-2-cyanoacrylate, methyl-2-cyanoacrylate, allyl acetate, allyl alcohol, allyl amine and the like.

comprising; reacting an olefin with mono functionalized and bis functionalized polar vinyl monomers in presence of nitrile ligated Pd-phosphinobenzene-sulphonate complex of formula (II) as catalyst.

The copolymer comprises at least one of the two of the above said functional group/groups.

The copolymers prepared in accordance with the invention are selected from:
i. poly(ethylene-ethyl-2-cynoacrylate)
ii. poly(ethylene-acrylonitrile)
iii. poly(ethylene-methyl acrylate)
iv. poly(ethylene-trifluoromethyl acrylate)
v. poly(ethylene-trifluoromethyl acrylic acid)

The insertion copolymerization of industrially relevant bis-substituted polar vinyl monomer such as cyano-acrylate (super glue) into linear ethylene chain is reported for the first time.

Accordingly, the process for co-polymerization comprises adding ethylene at 10 bar pressure into preheated reactor, cooling followed by addition of the solution of butylated hydroxyl toluene and mono or bis-substituted polar vinyl monomer in toluene, catalyst solution in DCM. The reactor was pressurized at about 5 bar and the mixture was stirred at a temperature of 80-95° C. for about 60-120mins until completion of the reaction. The excess solvent was vented out and the solid was dried under reduced pressure to obtain copolymer of which was characterized.

The present copolymers obtained with the process of the present invention can be used in a variety of applications such as in adhesives, binders, paints, printing ink, dyeing etc. The copolymers can be formed into fibers by the methods known in the art.

EXAMPLES

Following examples are given by way of illustration and therefore should not be construed to limit the scope of the invention.

General Methods and Materials

Unless noted otherwise, all manipulations of palladium complexes were carried out under an inert atmosphere using standard Schlenk or glovebox techniques. Toluene was distilled from sodium, diethyl ether and THF from sodium/benzophenone under argon. Acetonitrile and Methylene chloride were distilled on $CaH_2$. Ethylene (3.5 grade) supplied by, Acrylonitrile supplied by Alfa-Aeser and Ethyl-2-Cyonoacrylate supplied by Aldrich were used as received. MA and MMA supplied by Aldrich were distilled from 4.5° A linde molecular sieves. (COD)PdMeCl, [2-(2-methoxyphenyl)phosphino]benzenesulphonic acid, Acetone-dimer [({(P^O)Pd(Me)Cl}μ-Na)2]$^3$ (2) were synthesized following known procedures.

NMR spectra were recorded on a Brooker avance 400 spectrometre. $^1H$ and $^{13}C$ signal referenced to the solvent signal. Multiplicities are given as follows s: singlet, d: doublet, t: triplet, m: multiplet. High temperature NMR experiments of polyethylene were performed in o-dichlorobenzene at 120° C. Gel permeation chromatography of the polymers was recorded in 1,2,4-trichlorobenzene at 160° C. on a Viscotek GPC instrument equipped with triple detectors. The columns were calibrated with linear polyethylene standards and the reported molecular weights are with respect to polyethylene standards. MALDI-ToF-MS was performed on AB SCIEX TOF/TOF TM 5800 and Dithranol was used as a matrix.

Example 1

Synthesis of Pd-phosphinesulfonate-acetonitrile Complex a) Process 1: Direct Synthesis The sodium-salt of phosphinesulfonate ligand 1 (75.1 mg, 0.17 mmol) was mixed with cyclooctadiene (COD)-palladium-methylchloride (50 mg, 0.165 mmol, 1 equivalent) in Schlenk tube. Acetonitrile (30 ml) was added to this Schlenk tube and mixture stirred for 5 minutes to a clear solution. The clear solution was cannula filtered and the filtrate passed through celite bed. The bed was washed with 10 ml of acetonitrile (3×10 ml) and the filtrate was collected in Schlenk flask. The volatiles were evaporated in vacuum and the yellowish white powder was washed with diethyl ether (10 ml). The residue was dried for 3 hours in vacuum to produce complex 3 as yellowish white powder (88 mg, 0.15 mmol) in 91% yield. The complex was characterized using single crystal X-ray diffraction as depicted in FIG. 1.

b) Process II

Synthesis of acetone-dimer [({(P^O)Pd(Me)Cl}μ-Na)2]2 was reported by Thomas Ru nzi,et.al(*J. Am. Chem. Soc.* 2009, 131, 422-423.).; following which complex 2 was prepared in good yields. 65 mg (0.05 mmol) of complex 2, 20.4 mg (0.105 mmol, 2.05 equiv) of $AgBF_4$ was weighed and transferred to a Schlenk tube with magnetic needle. To this mixture 0.4 ml (10 mmol, 200 equiv.) of acetonitrile is added followed by 10 ml of dichloromethane. The reaction mixture was stirred for 2 hours in dark, after which the soluble fraction was cannula filtered into 50 ml Schlenk flask to give yellow colored solution. The Schlenk tube was washed with 5 ml of DCM and the soluble fraction cannula filtered. The combined filtrate was evaporated very slowly under reduced pressure to afford yellow crystals.

The yellow crystals are characterized by single crystal XRD. $^1H$ NMR (500 MHz, CDCl$_3$, 298 K): δ=8.18 (s, 1H), 7.59 (bs, 2H), 7.49 (t, $^3J_{H-H}$=7.53 Hz, 2H), 7.43 (m, 1H,), 7.24 (m, 2H), 7.00 (t, $^3J_{H-H}$=7.37 Hz, 2H), 6.90 (dd, $J_{H-H}$=3.3 Hz, 4.6 Hz, 2H), 3.61 (s, 6H), 2.11 (s, 6H), 0.19 (s, 3H, Pd-Me). $^{31}$PNMR (500 MHz, CDCl$_3$, 298 K): δ=21.1. $^{13}$C NMR(400 MHz, CDCl$_3$, 298 K): δ=160.4 (d, C$_1$), 137.8 (d, C$_a$), 134.3 (C$_h$), 133.3 (C$_j$), 130.1 (d, C$_d$), 128.2 (d, C$_c$), 127.9 (d, C$_f$), 120.6 (d, C$_k$), 6.4 (d, C$_g$), 115.6 (C$_m$), 111.3 (d, C$_i$), 55.3 (OCH$_3$), 2.43 (C$_{Me}$), −2.9 (Pd—CH$_3$). ESI-MS (+ve) m/z=544.97 [M-ACN+Na]$^+$.

The single crystal data and structural refinement is presented in below table-1.

TABLE 1

| Formula sum | C$_{25}$H$_{27}$N$_2$O$_5$PPdS |
|---|---|
| Formula weight | 604.93 g/mol |
| Crystal system | orthorhombic |
| Space-group | P b c a (61) |
| Cell parameters | a = 16.3061(7) Å b = 16.4145(7) Å |
| | c = 19.0195(8) Å |
| Cell ratio | a/b = 0.9934 b/c = 0.8630 c/a = 1.1664 |
| Cell volume | 5090.69(40) Å$^3$ |
| Z | 8 |
| Calc. density | 1.57846 g/cm$^3$ |
| RAll | 0.0497 |
| Wyckoff sequence | c62 |

Example 2

Ethylene Polymerization Using the Catalyst Solution

Ethylene polymerization was carried out in a 250 ml stainless steel high pressure reactor (Buechi) equipped with mechanical stirrer and heating/cooling jacket. Prior to the experiment, the reactor was heated in vacuum to 80° C. for 30 minutes, cooled to room temperature and filled with argon. Reactor was flushed with ethylene (3 times, 10 bars) and was charged with appropriate quantity of toluene under positive ethylene stream. Further, the reactor was pressurized to 5 bars and saturated with ethylene for 30 minutes at desired reaction temperature before it was cooled to room temperature. A solution of butylated hydroxyl toluene (37 mg, 0.16 mmol in 10 ml toluene) and catalyst 3 solution (12 mg, 20 μmol in 10 ml DCM) was introduced into the reactor at room temperature. The reactor was then pressurized to 5 bar with stirring until appropriate temperature (90-110° C.) (as specified in table 2) was reached within 5 minutes. The polymerization was carried out for 30 minutes, the excess ethylene was slowly vented off and the reactor allowed to cool down to room temperature. The resultant polymer was precipitated by adding acidified methanol. The precipitated polymer mass was filtered, washed several times with methanol and dried under reduced pressure at 55° C. for 12 hours or until constant weight was obtained. The resultant polyethylene was characterized using high temperature $^{13}$C NMR spectroscopy which clearly suggests existence of polyethylene with a typical CH$_2$ signal at 29.7 ppm. The reactivity of catalyst 3 in ethylene polymerization was tested and the results are summarized in table 2.

TABLE 2

Ethylene polymerization using complex 3

| Expt. No. | Catalyst (μmol in 10 ml DCM) | Solvent (100 ml) | Time min. | Temp. (° C.) | Yield (gm) | TOF(*$10^4$) mol of PE/ mol of Pd/h | Mol. Wt ($M_n$) |
|---|---|---|---|---|---|---|---|
| 1. | 7 | Toluene | 30 | 90 | 0.193 | 0.196 | |
| 2. | " | " | " | 95 | 1.464 | 1.49 | |
| 3. | " | " | " | 100 | 1.650 | 1.68 | 15.2*$10^3$ |
| 4. | " | " | " | 105 | 0.176 | 0.18 | |
| 5. | " | Xylene | " | 105 | 1.240 | 1.26 | |
| 6. | " | " | " | 110 | 0.180 | 0.18 | |
| 7[a]. | " | " | " | 100 | 1.56 | 1.59 | |

[a]= BHT (0.08 mmol) added

Example 3

Copolymerization of Ethylene-Methyl Acrylate

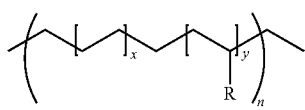

R = COOMe

The ethylene-methylacrylate copolymerization was carried out in a 250 ml stainless steel high pressure reactor (Buechi) equipped with mechanical stirrer and heating/cooling jacket. Prior to the experiment, the reactor was heated in vacuum to 80° C. for 30 minutes, cooled to room temperature and filled with argon. Reactor was flushed with ethylene (3 times, 10 bars) and charged with appropriate quantity of toluene under positive ethylene stream. The reactor was pressurized to 5 bars and was saturated with ethylene for 30 minutes at desired reaction temperature (90-110° C.) (as in table 3) before it was cooled to room temperature. A solution of butylated hydroxyl toluene (37 mg, 0.16 mmol in 10 ml toluene), calculated amount (as in table 3) of methylacrylate (diluted in 10 ml toluene) and catalyst solution (12 mg, 20 μmol in 10 ml DCM) were introduced into the reactor at room temperature. The reactor was then pressurized to 5 bars with stirring and appropriate temperature (95° C.) was reached within 5 minutes. The polymerization was carried out for 60 minutes, the excess ethylene slowly vented off and the reactor cooled to room temperature. The resultant solution was evaporated in vacuum to obtain solid mass, which was further dried under reduced pressure at 50° C. for 8 hours or until constant weight was obtained. The resultant copolymer was characterized using high temperature $^1$H NMR spectroscopy and methylacrylate incorporation was determined using the $^1$H NMR. $^1$H NMR (400 MHz, $C_2D_2Cl_4$, 343K) δ=3.69 (s, $OCH_3$), 2.36 (br., s, CH), 1.8-1.2 (br., m, $CH_2$).

The reactivity of catalyst 3 in copolymerization was tested and the results are summarized in table 3.

TABLE 3

Copolymerization of ethylene-methyl acrylate in presence of complex 3

| Expt. No. | Catalyst conc. | Ethylene pressure | MA Conc. (M/L) | Polymer yield (g) | TOF (*$10^3$) (mol of PE/mol of Pd/h) | % Incorporation[a] | Mol. Wt. ($M_n$)[b] | PDI |
|---|---|---|---|---|---|---|---|---|
| Run-1 | 20 μMol | 5 bar | 0.6 | 0.397 | 0.7 | 9.63 | 3100 | 1.3 |
| Run-2 | " | " | 1.2 | 0.337 | 0.6 | 15.6 | | |
| Run-3 | " | " | 2.5 | 0.282 | 0.5 | 25.8 | | |
| Run-4 | " | " | 5 | 0.253 | 0.4 | | | |

Conditions: total volume = 50 ml (toluene + monomer), Temperature = 95° C.,
[a]= determined by $^1$H NMR,

Example 4

Copolymerization of Ethylene-Acrylonitrile

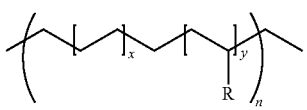

R = CN

The ethylene-acrylonitrile copolymerization was carried out in a 250 ml stainless steel high pressure reactor (Buechi) equipped with mechanical stirrer and heating/cooling jacket. Prior to the experiment, the reactor was heated in vacuum to 80° C. for 30 minutes, cooled to room temperature and filled with argon. Reactor was flushed with ethylene (3 times, 10 bars) and charged with appropriate quantity of toluene under positive ethylene stream. Further, the reactor was pressurized to 5 bars and saturated with ethylene for 30 minutes at desired reaction temperature (90-110° C.) (as in table 4) before it was cooled to room temperature. A solution of butylated hydroxyl toluene (37 mg, 0.16 mmol in 10 ml toluene), calculated amount of acrylonitrile (diluted in 10 ml toluene) and catalyst solution (12 mg, 20 μmol in 10 ml DCM) were introduced into the reactor at room temperature. The reactor was then pressurized to 5 bars with stirring and appropriate temperature (95° C.) was reached within 5 minutes. The polymerization was carried out for 60 minutes, the excess ethylene slowly vented off and the reactor cooled to room temperature. The resultant solution was evaporated in vacuum to obtain solid mass, which was further dried under reduced pressure at 50° C. for 8 hours or until constant weight was obtained. The resultant copolymer was characterized using high temperature $^1$H NMR spectroscopy and acrylonitrile incorporation is determined using the $^1$H NMR.
$^1$H NMR (400 MHz, $C_2D_2Cl_4$, 343K) δ=2.10 (br., s, CH), 1.6-1.2 (br., m, $CH_2$). The reactivity of catalyst 3 in copolymerization was tested and the results are summarized in table 4.

TABLE 4

Copolymerization of ethylene-acrylonitrile in presence of complex 3

| Expt. No. | Catalyst conc. | Ethylene pressure | ACN conc. (M/L) | Polymer yield (g) | TOF (*10³) (mol of PE/mol of Pd/h) | % Incorporation[a] | Mol. Wt. (Mn)[b] | PDI |
|---|---|---|---|---|---|---|---|---|
| Run-1 | 20 µMol | 5 bar | 0.24 | 0.130 | 0.23 | ND | 10000 | 2.06 |
| Run-2 | " | " | 0.12 | 0.126 | 0.22 | | | |
| Run-3 | " | " | 0.5 | 0.134 | 0.23 | | | |
| Run-4 | " | " | 1.2 | 0.068 | 0.2 | | | |

Conditions: Total volume = 50 ml (toluene + monomer), Temperature-95° C.,
[a] = determined by ¹HNMR,

Example 5

Copolymerization of Ethylene-Ethyl-2-Cyanoacrylate

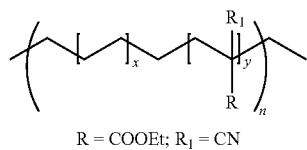

R = COOEt; R₁ = CN

The ethylene-ethyl-2-cynoacrylate copolymerization was carried out in a 250 ml stainless steel high pressure reactor (Buechi) equipped with mechanical stirrer and heating/cooling jacket. Prior to the experiment, the reactor was heated in vacuum to 80° C. for 30 minutes, cooled to room temperature and filled with argon. Reactor was flushed with ethylene (3 times, 10 bars) and charged with appropriate quantity of toluene under positive ethylene stream. Further, the reactor was pressurized to 5 bars and saturated with ethylene for 30 minutes at desired reaction temperature before it was cooled to room temperature. A solution of butylated hydroxyl toluene (37 mg, 0.16 mmol in 10 ml toluene), calculated amount (as per table 5) of ethyl-2-cynoacrylate (diluted in 10 ml toluene) and catalyst solution (12 mg, 20 µmol in 10 ml DCM) were introduced into the reactor at room temperature. The reactor was then pressurized to 5 bar with stirring and appropriate temperature (95° C.) reached within 5 minutes. The polymerization was carried out for 60 minutes, the excess ethylene was vented off and the reactor allowed to cool down to room temperature under argon. The resultant solution was transferred to a Schlenk flask with syringe and the volatiles were evaporated in vacuum to obtain solid mass, which was further dried under reduced pressure at 50° C. for 8 hours or until constant weight was obtained.

¹H NMR (500 MHz, $C_2D_2Cl_4$, 403 K): δ=4.46 (br., s, $OCH_2CH_3$), 2.89-2.30 (br., m, $CH_2$), 1.49 (br., s, $OCH_2CH_3$), 1.38 (br., s, $CH_2$). ¹³C NMR (500 MHz, $C_2D_2Cl_4$, 403 K): δ=165.1 (CO), 117.3-113.7(CN), 64.6 (C $OCH_2CH_3$), 45.7-43.2 ($C_{quaternary}$), 29.4 ($CH_2$), 13.6-12.9 ($OCH_2CH_3$). The reactivity of catalyst 3 in copolymerization was tested and the results are summarized in table 5.

TABLE 5

Copolymerization of ethylene-ethyl-2-cynoacrylate in presence of complex 3

| Expt. No. | Catalyst conc. | Ethylene pressure | ECA Conc. (M/L) | Polymer Yield (g) | TOF(*10³) (mol of PE/ mol of Pd/h) | % Incorporation[a] | Mol. Wt. (Mn)[c] | PDI |
|---|---|---|---|---|---|---|---|---|
| Run-1 | 20 µMol | 5 bar | 0.03 | 0.933 | 1.6 | 0.32 | 4700 | 1.5 |
| Run-2 | " | " | 0.06 | 0.902 | 1.6 | 2.09 | 8200 | 1.4 |
| Run-3[b] | " | " | 0.12 | 0.996 | 1.8 | 4.92 | 6700 | 1.7 |
| Run-4[b] | " | 1 bar | 0.06 | 0.468 | 0.8 | 6.51 | 6100 | 1.6 |
| Run-5[b] | " | 10 bar | 0.06 | 1.144 | 2.0 | 1.90 | 8300 | 1.5 |

Conditions: total volume = 50 ml (toluene + monomer), Temp –95° C.,
[a] = determined by 1HNMR,
[b] = monomer added after addition of catalyst solution.
[c] = determined by HT-GPC in 1,2,4-trichlorobenzene at 160° C.

Example 6

Similarly, a comparative experiment of example 5 was repeated with 20 µm of DMSO complex of type 3 as catalyst and Galvinoxyl (0.2 mmol) as radical inhibitor for the copolymerization of ethylene-ethyl-2-cynoacrylate and the observations are provided in the below table 6.

TABLE 6

Copolymerization of ethylene-ethyl-2-cynoacrylate in presence of complex 3 &DMSO complex of type 3

| Run | ECA (mol/L) | $C_2H_4$ (bar) | % Incorp.[b] | Yield (g) | Mn (10³ g/mol)[c] | Mw/Mn[c] | TOF (*10³) mol ($C_2H_4$)/ mol(Pd)/h | Tm° C. |
|---|---|---|---|---|---|---|---|---|
| Run-1 | 0.03 | 5 | 0.32 | 0.90 | 4.7 | 1.5 | 1.60 | 129.2 |
| Run-2 | 0.06 | 5 | 2.09 | 0.79 | 8.2 | 1.4 | 1.30 | 128.8 |
| Run-3 | 0.12 | 5 | 4.92 | 0.87 | 6.4 | 1.7 | 1.55 | 130.0 |

TABLE 6-continued

Copolymerization of ethylene-ethyl-2-cynoacrylate
in presence of complex 3 &DMSO complex of type 3

| Run | ECA (mol/L) | $C_2H_4$ (bar) | % Incorp.[b] | Yield (g) | Mn ($10^3$ g/mol)[c] | Mw/Mn[c] | TOF (*$10^3$) mol ($C_2H_4$)/ mol(Pd)/h | Tm° C. |
|---|---|---|---|---|---|---|---|---|
| Run-4 | 0.06 | 1 | 6.51 | 0.20 | 5.8 | 1.6 | 0.36 | 123.6 |
| Run-5 | 0.06 | 10 | 1.9 | 1.09 | 8.3 | 1.4 | 1.96 | 129.7 |
| Run-6[d] | 0.06 | 1 | 2.01 | 0.21 | 4.9 | 1.2 | 0.36 | ND |
| Run-7[e] | 0.06 | 1 | ND | 0.19 | ND | ND | 0.33 | ND |

[a]Reaction conditions: 3 = 20 μmol in DCM, toluene = 50 ml (Toluene + EGA); temperature = 95° C., time = 1 hour,
[b]ECA incorporation was determined by high temperature $^1$H NMR in $C_2D_2Cl_4$ at 130° C.;
[c]Determined by high temperature GPC at 160° C. in tri-chlorobenzene against PS standard;
[d]20 μm of DMSO complex of type 3 was used as catalyst;
[e]Galvinoxyl (0.2 mmol) was used as radical inhibitor;
ND = Not determined.

Example 7

Copolymerization of ethylene-trifluoromethyl acrylic acid

The ethylene-trifluoromethyl acrylic acid (TFMAA) copolymerization was carried out in a 50 ml glass high pressure reactor (Buechi-Mini clave) equipped with mechanical stirrer and heating/cooling jacket. Prior to the experiment, the reactor was heated in vacuum upto 80° C. for 30 minutes, cooled to room temperature and was filled with argon. The reactor was flushed with ethylene (3 times, 5-10 bars) and was charged with appropriate quantity of toluene under positive ethylene stream. Further, the reactor was pressurized to appropriate ethylene pressure (1 bar) and saturated with ethylene for 30 minutes at desired reaction temperature before it was cooled to room temperature. A solution of butylated hydroxyl toluene (37 mg, 0.16 mmol in 1 ml toluene), calculated amount of trifluoromethyl acrylic acid (diluted in 1 ml toluene) and catalyst solution 3 (12 mg, 20 μmol in 5 ml DCM) was introduced into the reactor at room temperature. The reactor was then pressurized to desired ethylene pressure (1 bar) with stirring and appropriate temperature (95° C.) was reached within 1-5 minutes. The polymerization was generally carried out for 60 minutes, the excess ethylene was slowly vented off and the reactor was allowed to cool down to room temperature under argon. The resultant solution was transferred to a Schlenk flask with syringe and the volatiles were evaporated in vacuum to obtain solid mass. The solid material thus obtained was washed thrice with diethylether (3×10 mL) and the insoluble solid was dried under reduced pressure for 4 hours. The insoluble copolymer fraction was thoroughly investigated using a combination of spectroscopic and analytical tools and the results are summarized in table 7. A proton resonance between 1.6 to 2.2 ppm can be ascribed to methylene protons in the copolymer back-bone. An IR spectrum of the copolymer revealed a characteristic $\Theta(C=O)$ at 1710 cm-1, that can be ascribed to acidic CO and is in line with earlier reports. Furthermore, a typical —OH band was observed at 3368 cm-1, which, together with CO band indicates the existence of carboxylic group in the copolymer. MALDI-ToF-MS spectrum of the copolymer also indicated TFMAA incorporation and various copolymer fragments (table 7 and FIGS. 2 A-C).

1H NMR (500 MHz, $C_2D_2Cl_4$, 403K): δ=2.2-1.6 (br., m, $CH_2$), 1.37 (br., s, $CH_2$).

TABLE 7

Copolymerization of ethylene-trifluoromethyl
acrylic acid in presence of complex 3[a]

| Run | TFMAA (mol/L) | $C_2H_4$ (bar) | % Incorp.[b] | Yield (g) | Mn ($10^3$ g/mol)[c] | Mw/Mn[c] |
|---|---|---|---|---|---|---|
| 1 | 0.06 | 1 | 0.73 | 0.37 | ND | ND |
| 2[d] | 3.0 | 1 | 3.0 | 0.07 | 2.8 | 1.2 |

[a]Reaction conditions: 3 = 20 μmol in DCM, toluene = 50 ml (Toluene + TFMAA); temperature = 95° C., time = 1 hour,
[b]TFMAA incorporation was determined by high temperature $^1$H NMR in $C_2D_2Cl_4$ at 130° C.;
[c]Determined by high temperature GPC at 160° C. in tri-chlorobenzene against PS standard;
[d]TFMAA incorporation was determined by high temperature $^1$H NMR in $C_6D_6$ + TCB (10:90) mixture at 120° C.

Table 8: MALDI-ToF-MS of copolymer of ethylene-trifluoromethyl acrylic acid CETxTFMAAy CETxTFMAAy indicates a copolymer chain of "x" ethylene units and "y" trifluoromethyl-acrylic acid units initiated by Pd-Me group. The following peaks were identified from a set of probabilities reported in table 8.

TABLE 8

| m/z | Copolymer |
|---|---|
| 518 | $CET_8TFMAA_2$ |
| 546 | $CET_9TFMAA_2$ |
| 742 | $CET_6TFMAA_4$ |
| 882 | $CET_6TFMAA_5$ |
| 938 | $CET_8TFMAA_5$ |
| 1022 | $CET_9TFMAA_6$ |
| 1246 | $CET_9TFMAA_7$ |

Figure 2A:
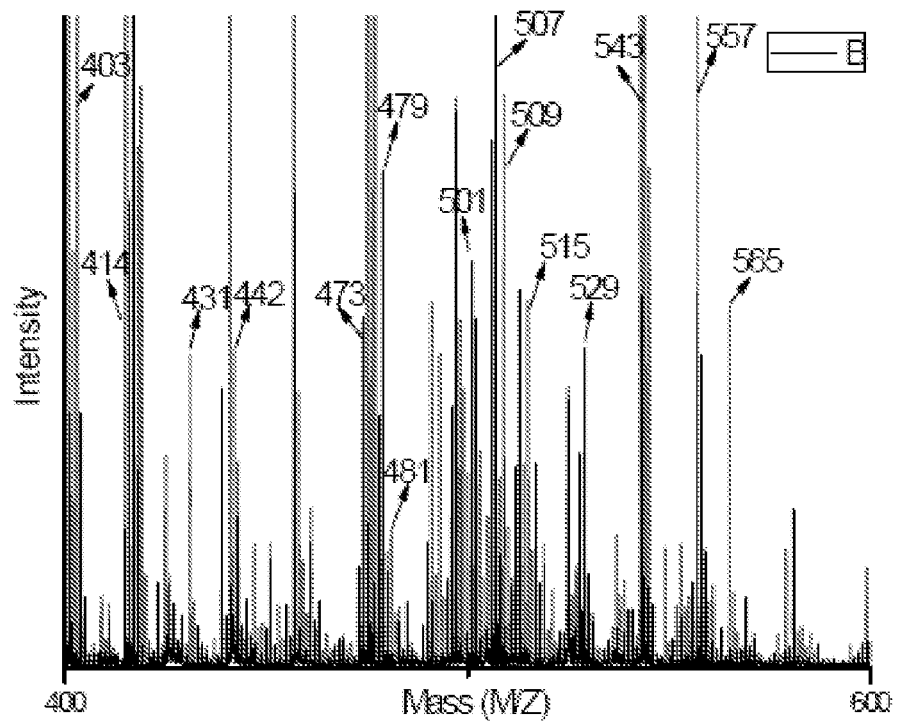
FIGS. 2A-C depict MALDI-ToF-MS spectra of a copolymer of ethylene and trifluoro-methyl acrylic acid (table 7, run-2).
Figure 2B:
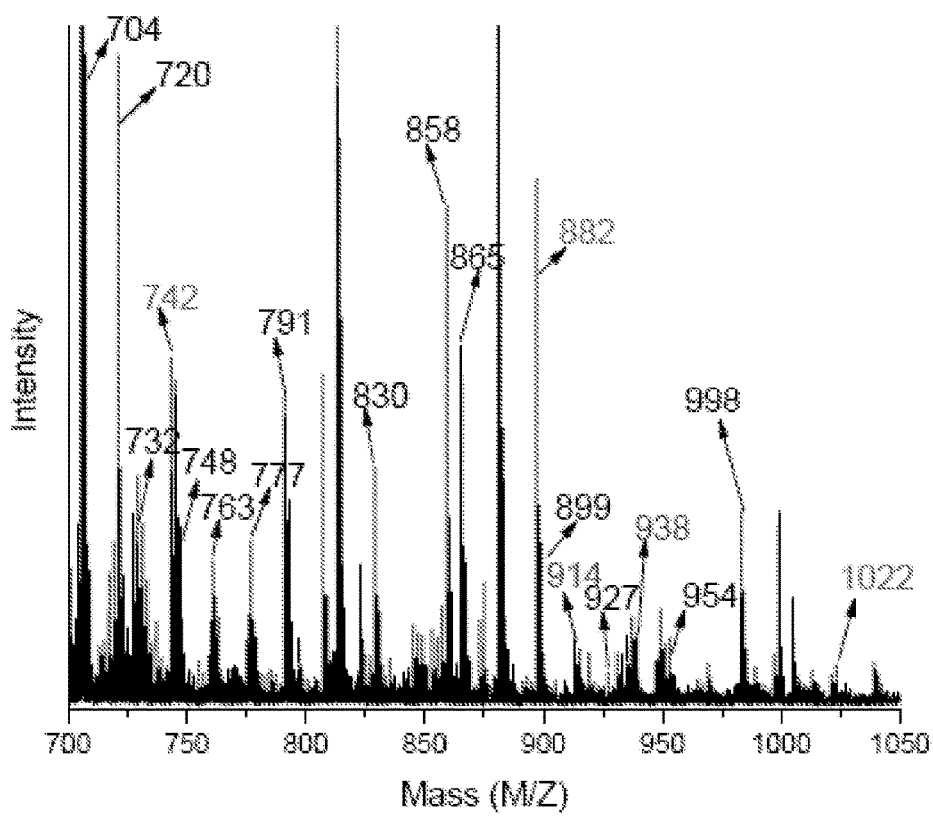
Figure 2C:
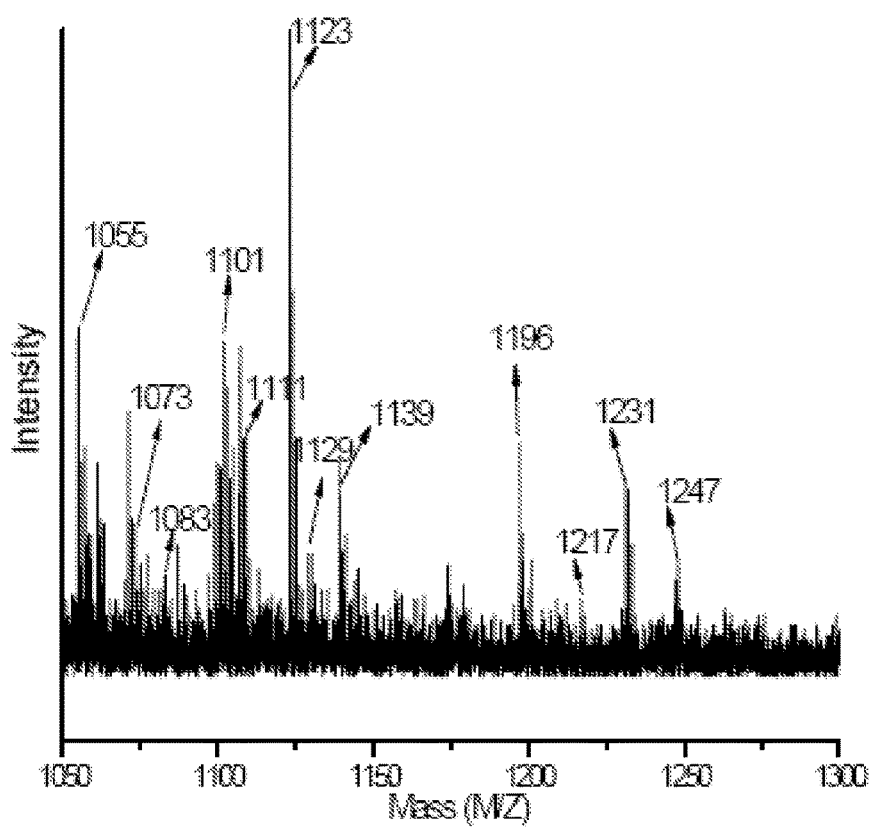

Apart from the fragments reported in above table, many peaks with a mass difference of 28 or multiples of 28 were detected (FIG. 2A).

Example 8

Control Experiments

Ethylene-ECA polymerization without catalyst (3)ECA is known to homopolymerize even in presence of traces of moisture and it is really difficult to avoid such ECA homopolymerization. As a control experiment, we investigated ECA-ethylene copolymerization in absence of catalyst 3. Exactly same polymerization protocol as mentioned in example 5 (5 bar ethylene pressure, 0.06 mol/L ECA, 95° C. for 1hr in presence of 35 mg of BHT) was followed, except that the catalyst (i.e. complex 3) was not added to the reactor.

Figure 3:
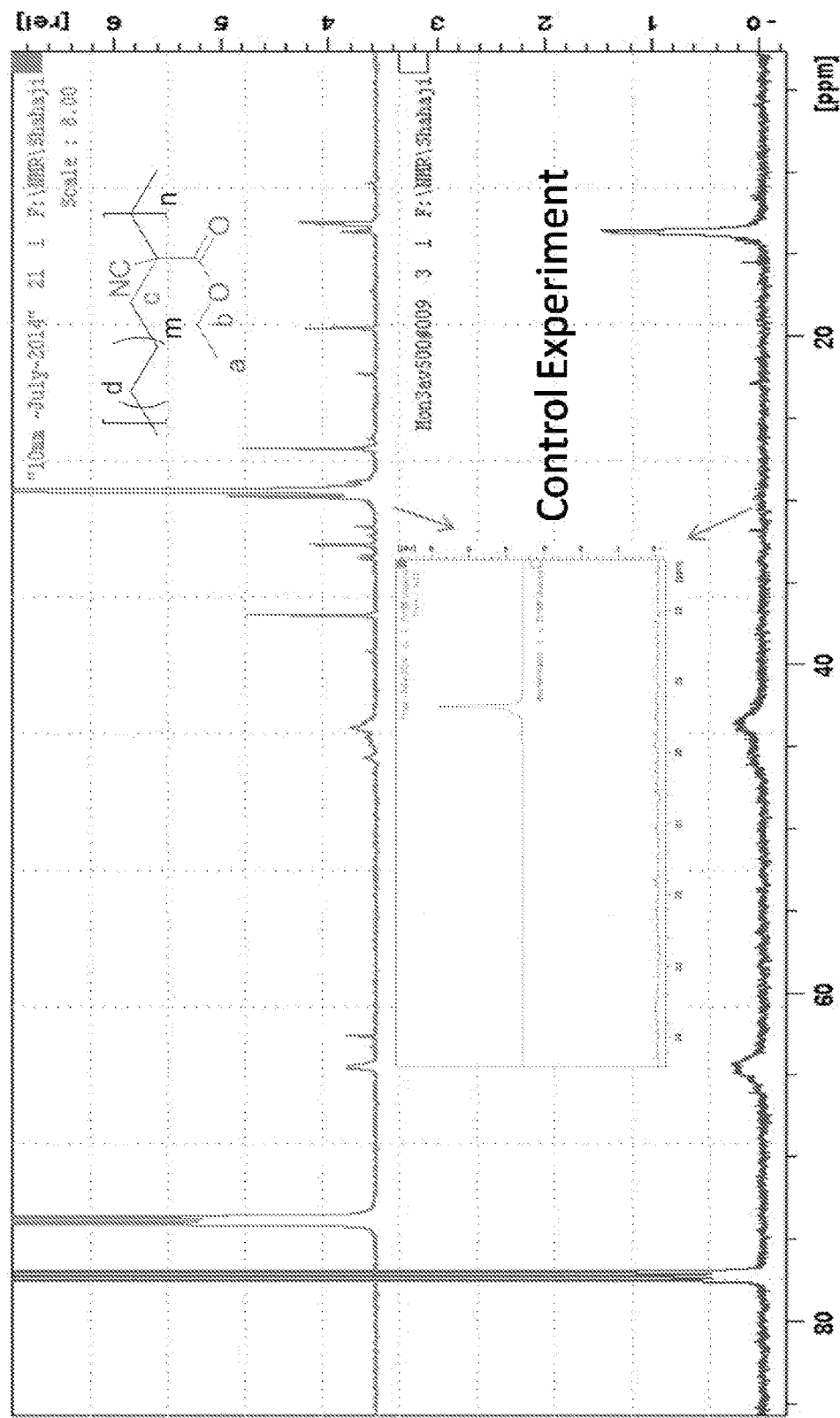
FIG. 3 depict $^{13}C$ NMR of ET-ECA copolymer (Table 5, 3-4) in $C_2D_2Cl_4$ at 393K (top) and ECA homopolymer in absence of complex 3 in $CDCl_3$ at room 298K (bottom).

This protocol led to the production of gel like material, which was dried and analyzed. The thus obtained polymer was found to be completely soluble in chloroform at room temperature and therefore the 13C NMR of above polymer was recorded in CDCl3 at room temperature. FIG. 3 depicts the comparison of copolymer obtained in run 4 (table 5) (top) and the homopolymer (bottom) obtained in this (control) experiment. As it is evident, no $^{13}C$ resonance could be observed in the typical polyethylene region (between 28-34 ppm) in control experiment sample, whereas 29.3 ppm was the major resonance in copolymer sample (from run 4). Thus, the absence of a matching carbon resonance at 29.3 ppm rules out formation of ethylene-ECA copolymer in absence of catalyst 3.

Example 9

Evaluating Existence of ECA Homopolymer in the Copolymer (From Run 4)

Figure 4:
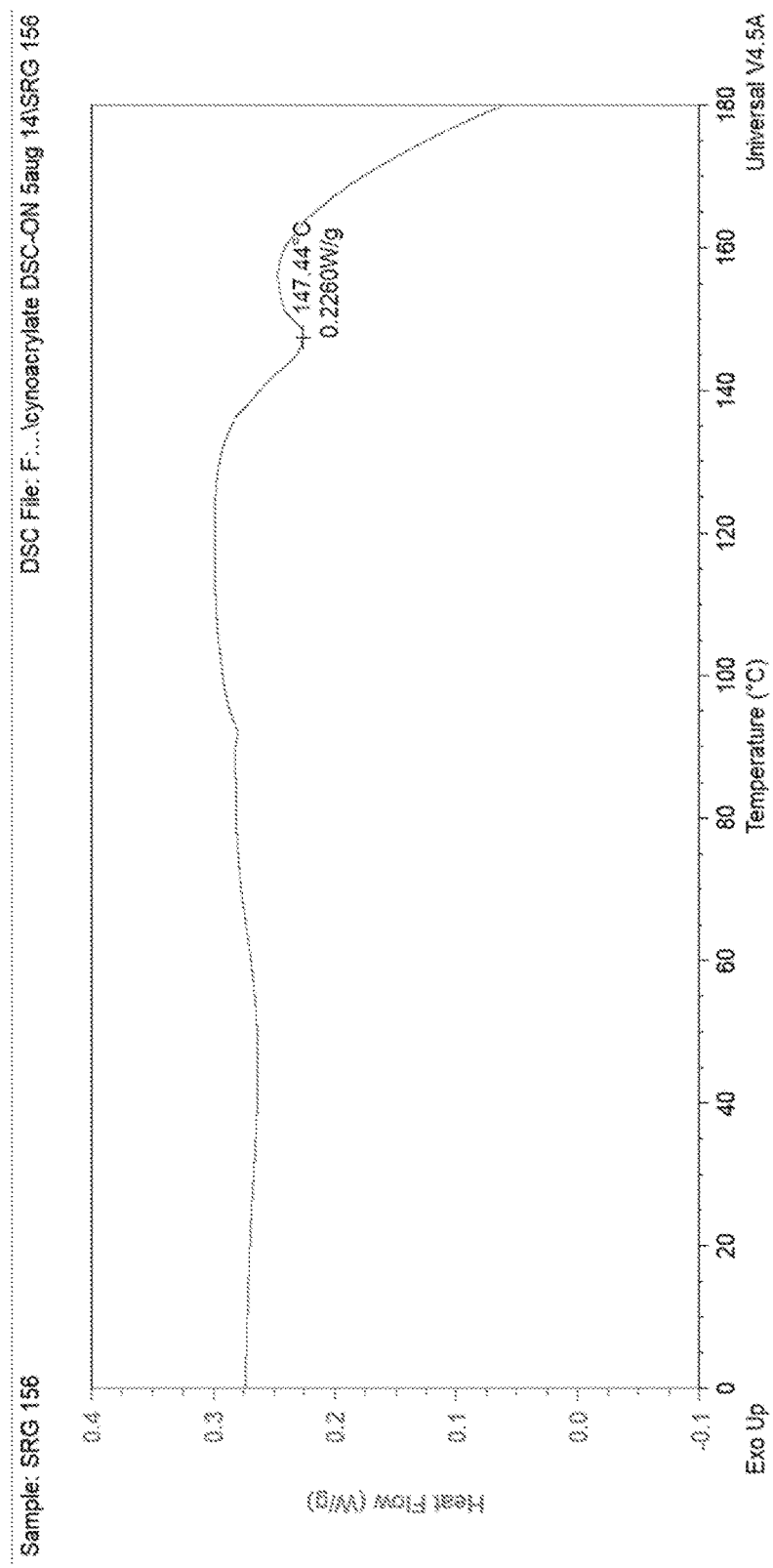
FIG. 4 depict DSC thermogram of ECA-homopolymer.
Figure 5:
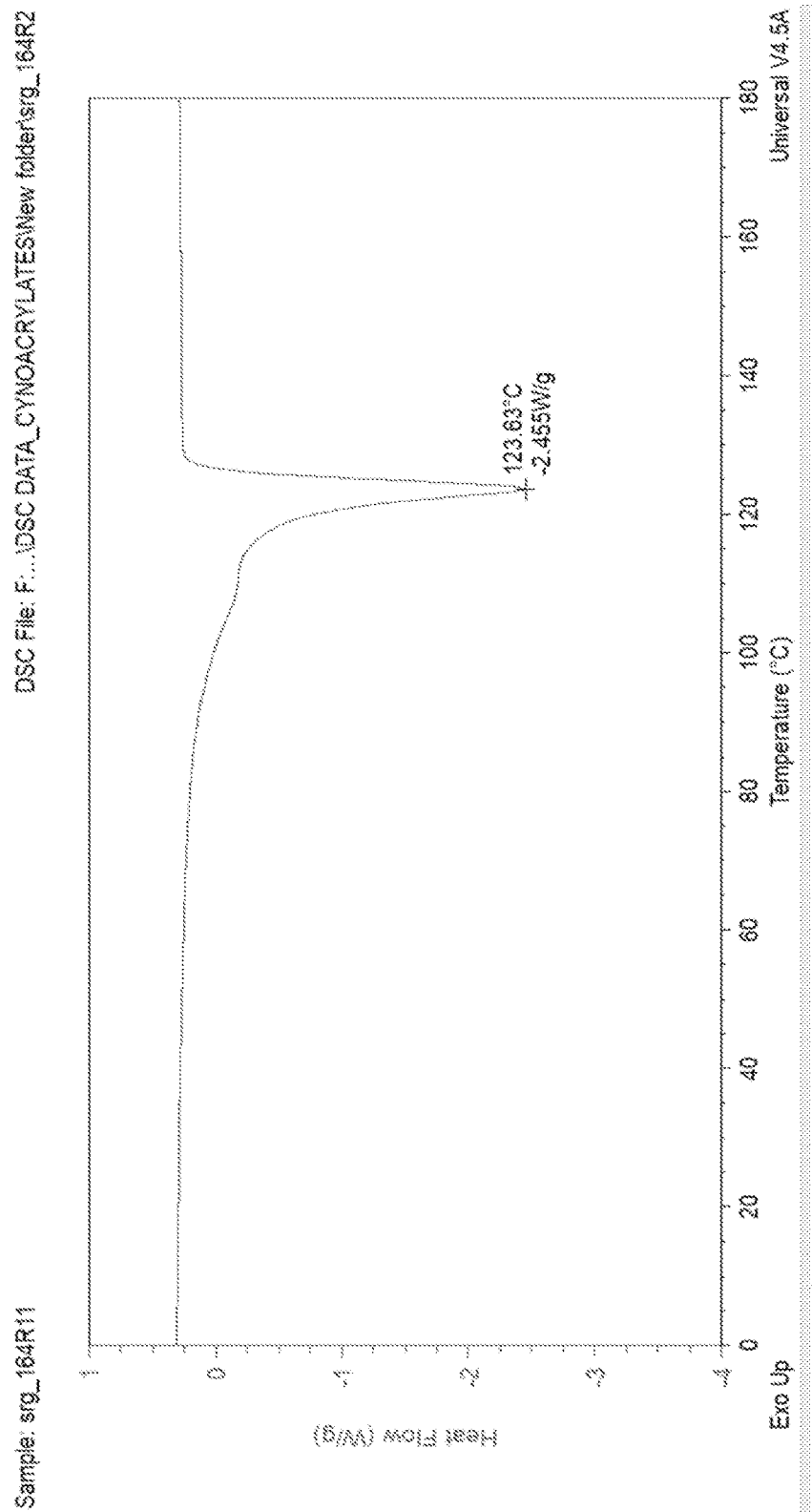
FIG. 5 depict DSC thermogram (2nd heating cycle) of ET-ECA copolymer (Table 5, run 3-4).
Figure 6:
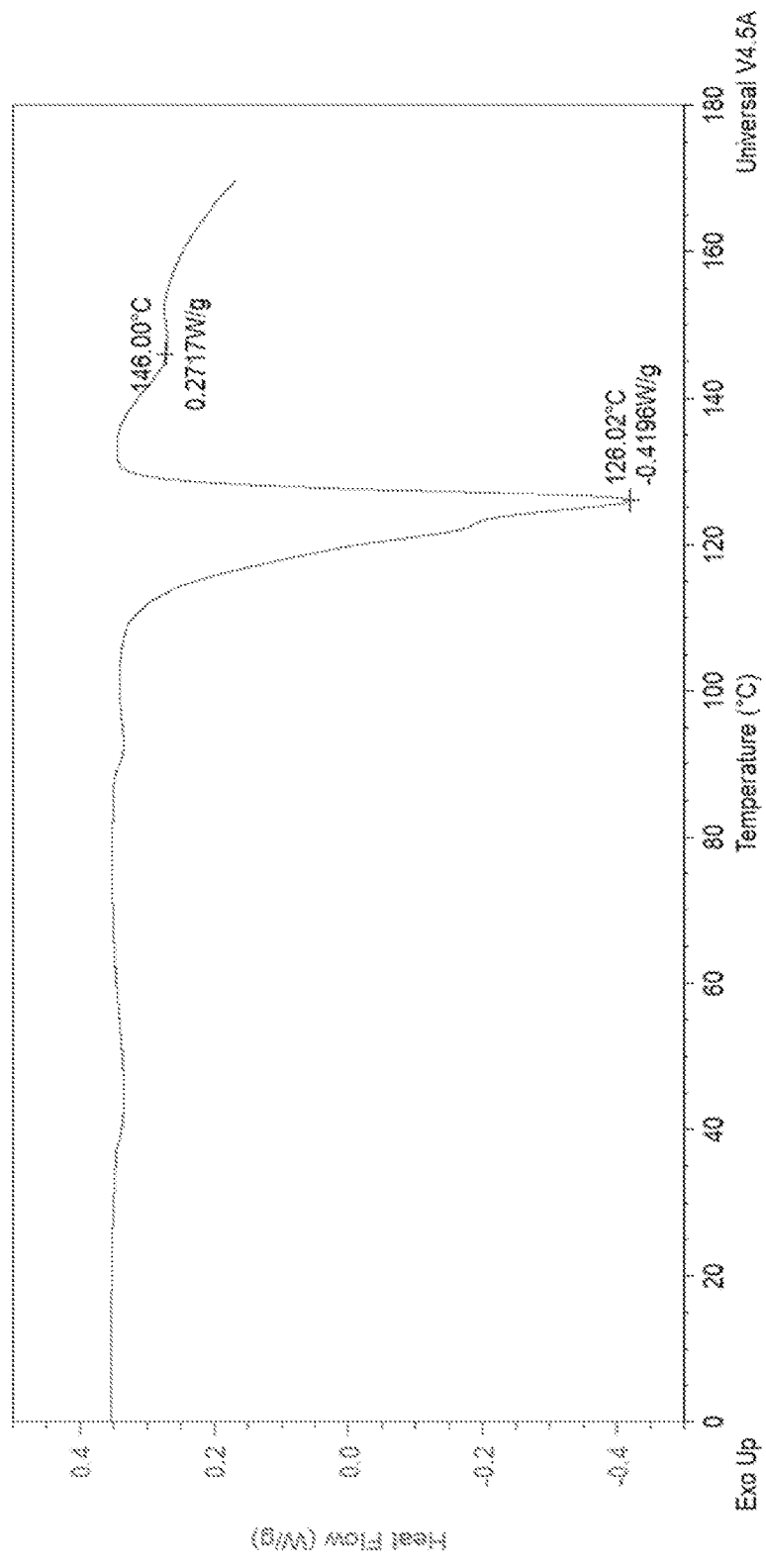
FIG. 6 depict DSC thermogram of a physical mixture of polyethylene+ECA-homopolymer.

The DSC scan of the ECA homopolymer (prepared as described in example 8) displayed a peak at 147° C. (FIG. 4), whereas, the copolymer sample from run 4 displayed a single peak at 123.6° C. (FIG. 5) and no peak at 147° C. could be detected. In addition to this, we have prepared a physical mixture of 93 mg of neat polyethylene (that was prepared using complex 3) and 7 mg of neat ECA homopolymer and analyzed it by DSC. The physical mixture clearly displayed two peaks, one at 126° C. and another at 146° C. (FIG. 6). These peaks can be easily ascribed to the PE and ECA homopolymer respectively. Thus, appearance of a single peak at 123.6° C. and absence of 147° C. peak in the copolymer sample (derived from run 3-4) clearly rules out the presence of ECA homopolymer and suggests incorporation of ECA in the copolymer.

Example 10

Existence of ET-ECA Copolymer

As described in example 5, the material obtained after copolymerization was thoroughly washed with chloroform (3 times) and the NMR was recorded. The high temperature NMR investigation indicated incorporation of ECA, and the data has been presented in table 5. The control experiment rules out the existence of homopolymer of ECA in the ethylene-ECA copolymer.

The copolymer sample in run 4 (table 5) was dissolved in trichlorobenzene (TCB) at 160° C. and was re-precipitated by adding methanol. The precipitate was dried and IR spectrum was recorded. The infrared spectrum revealed existence of CN vibration band at 2359 cm-1 and C—O stretching band at 1749 cm-1, indicating the incorporation of ECA in the re-precipitated copolymer sample.

Similarly, the copolymer sample with highest incorporation (table 5 run 4) was suspended in chloroform for 48 hours at room temperature. After 48 hours, the turbid solution was filtered and the solid obtained was dried in vacuum. IR spectrum of the dried copolymer displayed CN and CO (2359 cm-1 and 1749 cm-1 respectively) bands, confirming the incorporation of ECA in the ethylene-ECA copolymer.

TABLE 9

NMR data on relative bindging strengths of DMSO and acetonitrile in complex 3.

|  | Pd—C$\underline{H}_3$ | C$\underline{H}_3$CN | DMSO | $^{31}P$ |
|---|---|---|---|---|
| 3 | 0.18 | 2.10 | — | 21.13 |
| 3 + 1 eq. DMSO | 0.39 | 2.02 | 2.69 | 18.07 |

ADVANTAGES OF THE INVENTION

1. The present invention reports the novel Pd-phosphonebenzensulfonate complex with simple acetonitrile as a donor solvent.

2. The present invention uses cheap monomer ethylene which on insertion-copolymerisation process using the novel Pd-phosphonebenzenesulfonate-acetonitrile catalyst enhances the potential application of PE in adhesives, binders, paints, printing ink, dyeing etc. The prior art discloses the polymer of cyano-acrylate known as super glue which is commercially used in applications such as binders, adhesives etc. however, the method to polymerize this monomer uses radical reactions, which are uncontrolled and lead to undefined polymers. Furthermore; the monomer itself is costly compared to ethylene.

3. The insertion polymerization provides better controlled over polymer properties and those can be easily tuned. In addition to this, incorporation of ethylene into the polymer chain reduces the cost of final material.

We claim:

1. A one-step process for preparation of a complex of formula (I)

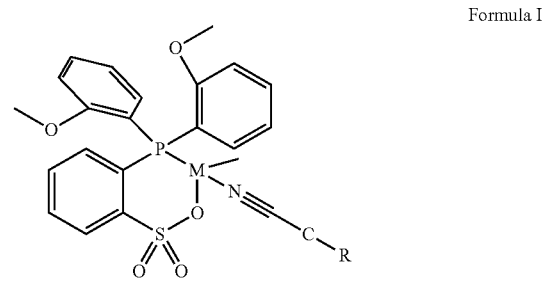

Formula I comprising:

mixing a sodium-salt phosphinesulfonate ligand and a reagent at 25-40°C. followed by adding acetonitrile at the same temperature to obtain the complex of formula (I), wherein M is Pd, Pt, Ni or Ru;

R is methyl;

the reagent comprises Pd, Pt, Ni or Ru; and the sodium-salt phosphinesulfonate ligand has a structure (1)

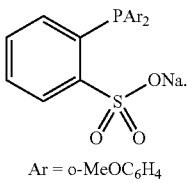

Ar = o-MeOC₆H₄

2. The process as claimed in claim 1, wherein the reagent is cyclooctadineyl-palladium-methylchloride, tetramethylethylenediamine-nickel-dimethyl, tetramethylethylenediamine-nickel-dichloride, tetramethylethylenediamine-palladium-methylchloride, tetramethylethylenediamine-platinum dimethyl, tetramethylethylenediamine-platinum-dichloride or cyclooctadienyl-ruthenium-dichloride.

3. A one-step process for preparation of a complex of formula (I)

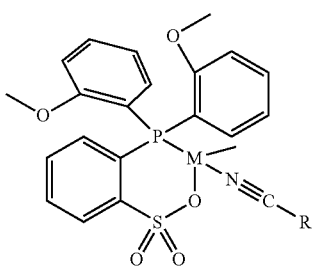

Formula (I)

comprising:
adding AgBF₄ to [({P^O)Pd(Me)Cl}μ-Na)₂]followed by adding acetonitrile and dichloromethane and stirring the mixture at 25-40°C. to obtain the complex of formula (I);
wherein
M is Pd; and
R is methyl.

4. A process of insertion copolymerization comprising:
preparing a complex of formula (I) by mixing a sodium-salt phosphinesulfonate ligand and a reagent at 25-40° C. followed by adding acetonitrile at the same temperature to obtain the complex of formula (I),

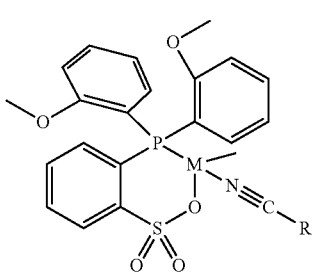

Formula (I)

wherein
M is Pd, Pt, Ni or Ru;
R is methyl:
the reagent comprises Pd, Pt, Ni or Ru; and
the sodium-salt phosphinesulfonate ligand has a structure (1)

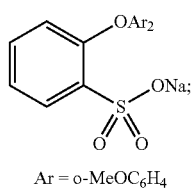

Ar = o-MeOC₆H₄ and reacting an olefin with a mono functionalized or bis functionalized polar vinyl monomer in the presence of the complex of formula (I) in a solvent at 45-110° C. and at 1-20 bars to obtain a copolymer of formula II;
wherein
the copolymer of formula (II) has the structure:

(A-B)n,                      Formula II wherein
n=10-10000;
A is a polymerized form of the olefin;
B is a polymerized form of the mono functionalized or bis functionalized polar vinyl monomer.

5. The process as claimed in claim 4, wherein the solvent is toluene, xylene, cyclohexane, or hexane.

6. The process as claimed in claim 4, wherein the concentration of the mono functionalized or bis functionalized polar vinyl monomer is in the range of 0.001 to 10.0 mol/L.

7. The process as claimed in claim 4, wherein the copolymer of formula II is:
a) poly(ethylene-othyl-2-cynoacrylate)
b) poly(ethylene-acrylonitrile)
c) poly(ethylene-methyl acrylate)
d) poly(ethylene-trifluoromethyl acrylate) or
e) poly(ethylene-trifluoromethyl acrylic acid).

8. The process as claimed in claim 4, wherein the olefin is ethene, propene, butene, or styrene.

9. The process as claimed in claim 4, wherein the mono functionalized or bis functionalized polar vinyl monomer is acrylate, acrylic acid, acrylonitrile, ethyl-2-cyanoacrylate, methyl-2-cyanoacrylate, trifluoromethyl acrylic acid, allyl acetate, allyl alcohol, or allyl amine.

* * * * *